United States Patent
Hippensteal

(10) Patent No.: US 10,898,350 B2
(45) Date of Patent: Jan. 26, 2021

(54) DYNAMIC LINEAR ADJUSTABLE PROSTHETIC

(71) Applicants: UNIVERSITY OF SOUTH CAROLINA, Columbia, SC (US); PRISMA HEALTH—UPSTATE, Greenville, SC (US)

(72) Inventor: Alan Robert Hippensteal, Greenville, SC (US)

(73) Assignees: University of South Carolina, Columbia, SC (US); Prisma Health—Upstate, Greenville, SC (US)

(*) Notice: Subject to any disclaimer, the term of this patent is extended or adjusted under 35 U.S.C. 154(b) by 35 days.

(21) Appl. No.: 15/778,734

(22) PCT Filed: Nov. 18, 2016

(86) PCT No.: PCT/US2016/062676
§ 371 (c)(1),
(2) Date: May 24, 2018

(87) PCT Pub. No.: WO2017/091456
PCT Pub. Date: Jun. 1, 2017

(65) Prior Publication Data
US 2018/0338844 A1    Nov. 29, 2018

Related U.S. Application Data

(60) Provisional application No. 62/386,260, filed on Nov. 24, 2015.

(51) Int. Cl.
*A61F 2/64* (2006.01)
*A61F 2/62* (2006.01)
(Continued)

(52) U.S. Cl.
CPC .............. *A61F 2/70* (2013.01); *A61F 2/60* (2013.01); *A61F 2/601* (2013.01); *A61F 2/64* (2013.01);
(Continued)

(58) Field of Classification Search
CPC ........ A61F 2002/502; A61F 2002/5084; A61F 2002/74–748
(Continued)

(56) References Cited

U.S. PATENT DOCUMENTS 4,883,493 A    11/1989  Martel et al.
5,800,557 A     9/1998  Elhami
(Continued)

FOREIGN PATENT DOCUMENTS

RU    1821177        6/1993
SU    1821177 A1  *  6/1993  ............... A61F 2/60
(Continued)

OTHER PUBLICATIONS

Gallaby, Retractable Prosthesis for Transfemoral Amputees Using Series Elastic Actuators and Force Control, arXiv:1511.09402v1 [cs.Ro] Nov. 30, 2015.
(Continued)

*Primary Examiner* — David H Willse
(74) *Attorney, Agent, or Firm* — Dority & Manning, P.A.

(57) ABSTRACT

A prosthesis with controlled linear motion and methods for adapting the device to multiple amputation points are described. The device is designed to shorten during the swing phase to prevent striking the surface of the ground, and extend at the beginning and end of the swing to provide forward propulsion and begin to transfer bodyweight load from the opposing leg. The prosthesis includes an actuator to provide linear motion, a battery, sensors, and a controller.

22 Claims, 6 Drawing Sheets

(51) Int. Cl.
*A61F 2/70* (2006.01)
*A61F 2/60* (2006.01)
*A61F 2/68* (2006.01)
*A61F 2/76* (2006.01)
*A61F 2/50* (2006.01)
*A61F 2/74* (2006.01)

(52) U.S. Cl.
CPC ................ *A61F 2/644* (2013.01); *A61F 2/68* (2013.01); *A61F 2/76* (2013.01); *A61F 2002/502* (2013.01); *A61F 2002/5006* (2013.01); *A61F 2002/5018* (2013.01); *A61F 2002/5033* (2013.01); *A61F 2002/5036* (2013.01); *A61F 2002/5073* (2013.01); *A61F 2002/5084* (2013.01); *A61F 2002/6854* (2013.01); *A61F 2002/701* (2013.01); *A61F 2002/704* (2013.01); *A61F 2002/74* (2013.01); *A61F 2002/762* (2013.01); *A61F 2002/764* (2013.01); *A61F 2002/7615* (2013.01); *A61F 2002/7625* (2013.01); *A61F 2002/7635* (2013.01)

(58) Field of Classification Search
USPC .......................................................... 623/35
See application file for complete search history.

(56) References Cited

U.S. PATENT DOCUMENTS

| | | | |
|---|---|---|---|
| 6,302,918 | B1 | 10/2001 | Grammas |
| 7,314,490 | B2 | 1/2008 | Bedard |
| 7,736,394 | B2 | 6/2010 | Bedard et al. |
| 8,231,687 | B2 | 7/2012 | Bedard et al. |
| 8,287,477 | B1 | 10/2012 | Herr et al. |
| 8,551,184 | B1 | 10/2013 | Herr |
| 8,628,585 | B2 | 1/2014 | Harris et al. |
| 9,084,689 | B2 | 7/2015 | Herr |
| 9,149,370 | B2 | 10/2015 | Herr et al. |
| 9,358,137 | B2 | 6/2016 | Bedard et al. |
| 9,687,363 | B2 | 6/2017 | Herr |
| 10,299,943 | B2 | 5/2019 | Clausen et al. |
| 10,406,000 | B2 | 9/2019 | Gao et al. |
| 10,476,347 | B2 | 11/2019 | Wang |
| 2002/0052663 | A1* | 5/2002 | Herr .......................... A61F 2/70 623/24 |
| 2007/0162152 | A1 | 7/2007 | Herr |
| 2009/0037000 | A1 | 2/2009 | Frye |
| 2014/0324190 | A1 | 10/2014 | Ossur |
| 2015/0202057 | A1* | 7/2015 | Zahedi ................. A61F 2/6607 623/26 |

FOREIGN PATENT DOCUMENTS

| | | | | |
|---|---|---|---|---|
| WO | WO 00/74610 A1 | * | 12/2000 | ............... A61F 2/62 |
| WO | WO 2015/073182 A1 | * | 5/2015 | ............... A61F 2/66 |

OTHER PUBLICATIONS

Waycaster, Design of a Powered Above Knee Prosthesis Using Pneumatic Artificial Muscles., Department of Mechanical Engineering, the University of Alabama, 2010.
PCT International Search Report re PCT/US2016/062676, dated Nov. 18, 2016.
PCT Written Opinion of the International Searching Authority re PCT/US2016/062676, dated Jan. 19, 2017.
PCT Preliminary Report on Patentability re PCT/US2016/062676, dated Jan. 8, 2018.

\* cited by examiner

DYNAMIC LINEAR ADJUSTABLE PROSTHETIC

CROSS REFERENCE TO RELATED APPLICATION

This application claims filing benefit of U.S. Provisional Patent Application Ser. No. 62/386,260 having a filing date of Nov. 24, 2015, which is incorporated herein by reference.

BACKGROUND

Human gait requires complex and dynamic control of multiple muscles and joints to allow mobility while providing stability and minimizing the energy cost of ambulation. Analysis of human ambulation is described using the gait cycle, which is divided into a stance phase and a swing phase for each foot during each step. During the stance phase the foot is in contact with the ground providing support of the body weight. The primary power for propulsion occurs during late stance phase when the body is accelerated over the foot.

The swing phase follows the stance phase and describes the period during which the foot is advanced over the ground. A complex series of joint movements in both the trunk and extremities combine during ambulation to minimize the displacement of the center of gravity and maximize the efficiency of gait. The determinants of gait involve movements of the pelvis, hip, knee, and ankle, acting together to minimize the displacement of the center of gravity while walking. A primary effect of these movements is an alternating lengthening and shortening of the distance between the end of the leg (e.g., the foot) and the body.

Following lower extremity amputations the structures that are lost decrease the amputee's mobility and function. The energy cost of daily activities is greatly increased. Safety is decreased and the amputee often needs assistance in daily care. Many amputees also have compromised cardiac and pulmonary function that limits strength and endurance. Loss of even a distal portion of an extremity results in significant impairment. Proximal amputations that involve loss of multiple joints and muscles have an even higher cost.

There are approximately 7 million lower-extremity amputees in the world, of which 30% are above the knee and 70% below the knee. Amputation may result from trauma such as accidents or war, or from disease such as diabetes. Amputating sections of a lower limb reduces both the control and efficiency of ambulation with successively higher amputations having greater effect and resulting in a high difficulty of ambulation, preventing some users from participating in daily activities.

Prostheses are used whenever possible to provide ambulation and aesthetic norms and assist wearers to return to work, travel, and participate in activities. Lower extremity prosthetics typically include a socket to fit over the terminal portion of the remaining extremity, an internal or external elongated structural component extending from the socket, and a terminal device such as a foot. These components can be fabricated separately using various materials or combined in a single monocoque structure.

Modern prosthetics attempt to simulate physiological mechanics of the replaced anatomy. In particular, current approaches to the design of prosthetics attempt to replace the lost anatomical structures with mechanical representations focusing mainly on anatomic similarity while attempting to mimic physiological motions primarily using rotation around joints. Prosthetic joints often include control systems to improve safety and efficiency. Some prosthetics use a powered controlled motion to provide rotation of a joint. For instance, joints can be designed to rotate freely or against resistance, and the amount of resistance applied across the joint can be variable or fixed and can be preset or actively controlled. Lower limb prosthetics may also incorporate a passive resistance to absorb the heel-strike impact during gait.

Prosthetics that incorporate more sophisticated motion and control systems such as controlled resistance and/or powered joint rotation will also exhibit an increase in weight, complexity and cost over simpler but less effective devices. Moreover, the addition of more sophisticated mechanics often creates secondary problems. For instance, artificial knees can flex unexpectedly causing falls and even the most sophisticated prosthetics are still not capable of restoring the mechanical propulsion of natural anatomical structures.

What is needed in the art is a prosthesis that provides improved ambulatory efficiency and functionality without excessive complexity or introduction of additional fall risk to the wearer.

SUMMARY

According to one embodiment, disclosed is a prosthetic including a distal end, a proximal end at a distance from the distal end, and an actuator between the distal and proximal ends, the actuator being configured to modify a distance between the distal end and the proximal end and thereby lengthen or shorten the prosthetic. In one particular embodiment, the prosthetic is a lower limb prosthetic Also disclosed is a method for forming a prosthetic. For instance, a method can include placing an actuator in communication with a prosthetic, the actuator controlling a length of the prosthetic such that a distance between the prosthetic ends can be automatically modified so as to lengthen or shorten the prosthetic during use.

DETAILED DESCRIPTION

It is to be understood by one of ordinary skill in the art that the present discussion is a description of exemplary embodiments only, and is not intended as limiting the broader aspects of the present disclosure. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

A prosthesis is disclosed herein that can include a linear actuator for controlled linear motion and automatic length adjustment. In one particular embodiment, the prosthesis can be designed for a lower limb, but it is not limited to this embodiment. Beneficially, the prosthesis can automatically adjust in total length during use, for instance during each step while walking, climbing stairs, standing, running, etc. A prosthesis can also retract while sitting in one embodiment.

The prosthesis uses a controlled linear motion to modify the length of the prosthesis which can improve the safety and efficiency of ambulation. More specifically, the prosthesis can use a linear extension/retraction mechanism, e.g., a telescopic system, to provide a controlled, cyclic lengthening and shortening of the prosthesis. In one particular embodiment, the automatic length adjustment capability of the prosthesis can minimize or even completely remove the need to incorporate an artificial rotation-based joint, e.g., a knee joint, in a prosthetic.

The automatic linear adjustment of a prosthetic can be adapted to many different prosthetic types depending on the level of amputation and the function of the amputee. Controlled and automatic linear motion can allow the prosthetic to have an optimized length throughout the entire gait cycle, providing clearance for the foot to swing forward over the ground during swing phase and lengthen in preparation for heel strike. The ability to actively lengthen and shorten the prosthetic during gait can not only improve gait so as to appear more natural, but can also eliminate or reduce the need for artificial rotation-based joints, thus reducing or eliminating the risk of joint buckling that can cause a fall.

Figure 1:
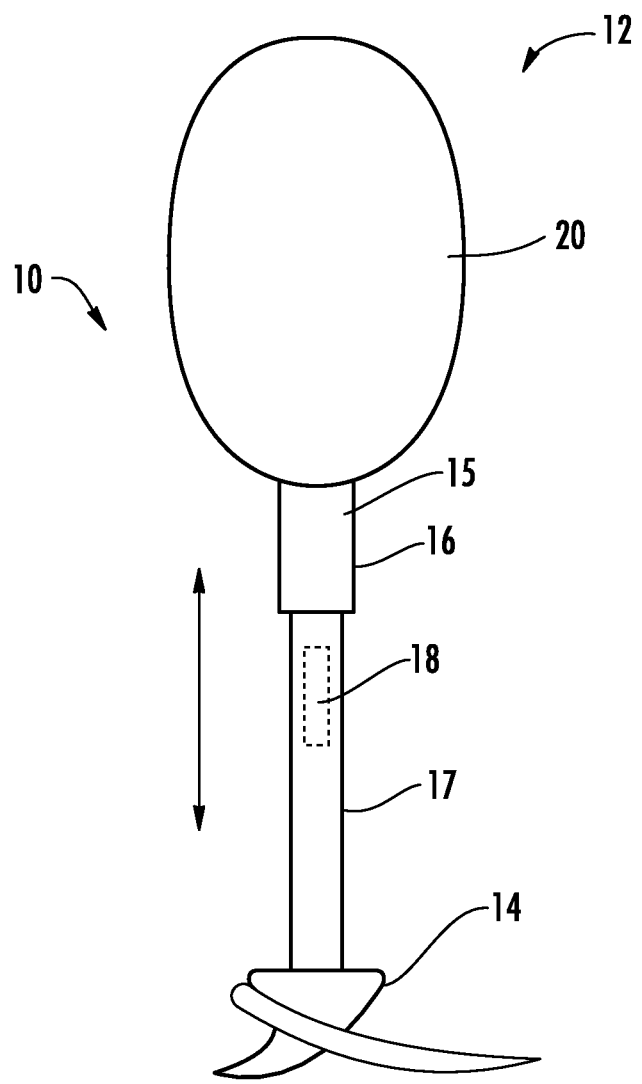
FIG. 1 shows a below-knee prosthetic using a telescoping actuator incorporated into the pylon of the prosthetic providing a direct lengthening and shortening of the prosthetic along the axis.

FIG. 1 illustrates one embodiment of a prosthetic 10 as disclosed herein. In general, a prosthetic can include a proximal end 12, a distal end 14, separated by a distance, e.g., by a segment 16 between the proximal and distal ends, as shown. In general, the proximal end 12 can include a socket 20 that can attach at the amputation site. A prosthetic 10 can include any suitable socket 20 and can be compatible with both standardized and non-standardized sockets as is known.

A segment 16 between the two ends of the prosthetic 10 can be configured to extend and retract under the control of an actuator 18 so as to lengthen or shorten the entire prosthetic. In one embodiment, the extension and retraction of the segment 16 can be in alignment with the long axis of the prosthetic 10, as indicated by the directional arrow on FIG. 1. The actuator 18 can be in any suitable configuration, orientation, and location so as to control and direct the overall length of the prosthetic. For example, the actuator 18 can be oriented along the long axis of the device and have a direct or indirect connection with the segment 16 so as to activate length modification of the segment 16.

Actuator 18 can promote and control linear action along a prosthetic according to any mechanism including but not limited to ballscrew drive, direct electric drive, hydraulic, pneumatic, or mechanical. For instance, an actuator 18 can provide a motive force to the prosthetic through any number of mechanical components working in concert with one another such as cams, cranks, levers and screws. The actuator 18 can be aligned with the direction of movement of the segment 16, for instance in the case of a hydraulic or pneumatic piston actuator, but can optionally be oriented at an angle to the long axis of the prosthetic 10. Moreover, and as discussed further herein, a prosthetic 10 can include a single actuator or multiple actuators as well as single or multiple extensible segments. The prosthetic can optionally include springs, pressurized air or fluid mechanisms, shock absorbers, or the like that can reduce the effective force of the linear drive felt by the wearer and/or the necessary force applied by the use to operate the actuator and bring about the desired lengthening or shortening of the prosthetic.

Though illustrated as being generally axial with the overall orientation of the prosthetic 10, it should also be understood that the motion provided by the actuator 18 to the segment 16 can be directly in-line with the long axis of a prosthetic or at an angle to the long axis of a prosthetic. The direction of motion can generally depend upon the particular design of the prosthetic as well as the orientation of the particular segment that will exhibit the length modification during use. However, in any case, the actuator is configured to be capable of lengthening and shortening the overall length of the prosthetic and this action is not to be confused with rotational-type actuators in which a first lengthening component on one side of the device is coupled with a shortening component on an opposite side of the device. The lengthening/shortening components are designed to work in concert with one another so as to provide a rotational motion to the prosthetic. While the disclosed actuators can in some embodiments also provide a rotational motion (discussed in more detail below) as a secondary feature, the actuators are primarily configured to lengthen and shorten the entire length of the prosthetic.

In the embodiment illustrated in FIG. 1, segment 16 can include a first portion 15 and a second portion 17 that are slidably engaged with one another such that under the control of the actuator 18, the segment can lengthen and shorten as needed. For instance, the length of the prosthetic 10 can be actively controlled during the stance phase of gait to support the body weight and minimize the displacement of the center of gravity. This can decrease the energy use of the wearer necessary for ambulation. Propulsion can be provided by lengthening the segment 16 at the end of the stance phase. This added push provided by the lengthening of the segment 16 by the actuator 18 can also decrease the energy required by the wearer during ambulation.

Beneficially, the extent of the extension and contraction of the segment 16 as well as the pattern of the motion (e.g., the speed of extension and contraction, etc.) can be individualized to meet the wearer's needs and can be adjusted as necessary to provide maximum efficiency, ease of use, and safety. Accordingly, a prosthetic can include or be configured to communicate with sensors and control systems as well as being capable of accepting manual inputs to control the motion of the device.

A control system can be utilized to instruct the actuator(s) 18 to lengthen or shorten the prosthesis 10 as necessary to prevent foot strike during the swing phase, to provide impact dampening during heel strike, and to provide propulsion at the end of the gait. Moreover, the control system can instruct the actuator 18 to retract the segment 16 to the full extent possible as desired, for instance when sitting. Optionally, a system can include a locking mechanism to allow the prosthetic to be held in place at any desired length, for instance to provide static support during an upright stance. A control system can be in wired or wireless communication with an actuator 18. For instance, a control system (or portions thereof) can be carried on the prosthetic 10 or optionally can be carried by a wearer, for instance in a bag, attachable to a belt, etc.

A control system can be powered by a battery that may in one embodiment be rechargeable. The input to a control system may include but not be limited to motion and position sensors located on the patient's body and/or on the prosthesis. Position sensors can utilize, switches, radar, sonar, optical devices that utilize visible, ultraviolet, or infrared light (e.g., lasers), accelerometers, gyroscopes, or other means to determine aspects for use during ambulation including, without limitation, the distance from the prosthesis (e.g., a point on the distal end 14) to the ground, an angle between the segment 16 and the ground, walking speed, etc. A control system can utilize force sensors, for instance to determine an impact force with the ground and modify the speed and/or force of an extension of the segment 16.

Input such as a wearer's weight, height, gait length, etc. can be manually input to a control system for instance by use of a wired or wirelessly attachable keyboard, button or slider. Wireless communication can be via Bluetooth®, wifi, or other known multi-wavelength signal standards.

Any suitable prosthetic foot can be included at the distal end 14 and utilized in conjunction with the system. Various feet are commonly known in the art and can range from simple rubberized tips to complex anatomically similar feet that mimic organic range of motion. Flexible materials can also be used to reduce impact and simulate rotation around an ankle. The disclosed prosthesis is compatible with these and other feet known in the art, as well as non-standardized feet.

The materials used to form a prosthetic may include those typically used in the art. By way of example and without limitation, structural components may include fiber-reinforced plastic, titanium, steel, aluminum, and/or alloys commonly used in the art.

A prosthesis may include passive impact dampeners such as dashpots and springs, embodied by parallel or sequential coiled springs, eddy current dampers with one-way valves, or rubber bushings as are generally known. The prosthesis may also be wrapped in a flesh-simulant such as a polymer, rubber, or combination thereof standard in the art.

FIG. 1 illustrates a below-knee prosthetic 10. When utilizing a traditional, non-adjustable prosthetic, a below-knee amputee needs to flex at the hip and knee to provide clearance for the prosthetic foot during the swing phase of gait. These motions increase the energy cost of ambulating. These excess movements can be eliminated by the dynamic adjustment capabilities of the disclosed prosthetics.

Users with amputations below the knee can eliminate excess movements by the dynamic and automatic shortening and lengthening of the prosthetic that is provided by the actuator 18 in communication with the adjustable segment 16. Users may also benefit from propulsion at the end of the gait by actively lengthening the prosthesis to provide propulsion. This added "push" at the end of the stance phase corresponds to the propulsion provided naturally by flexing the foot and calf muscles.

Figure 2:
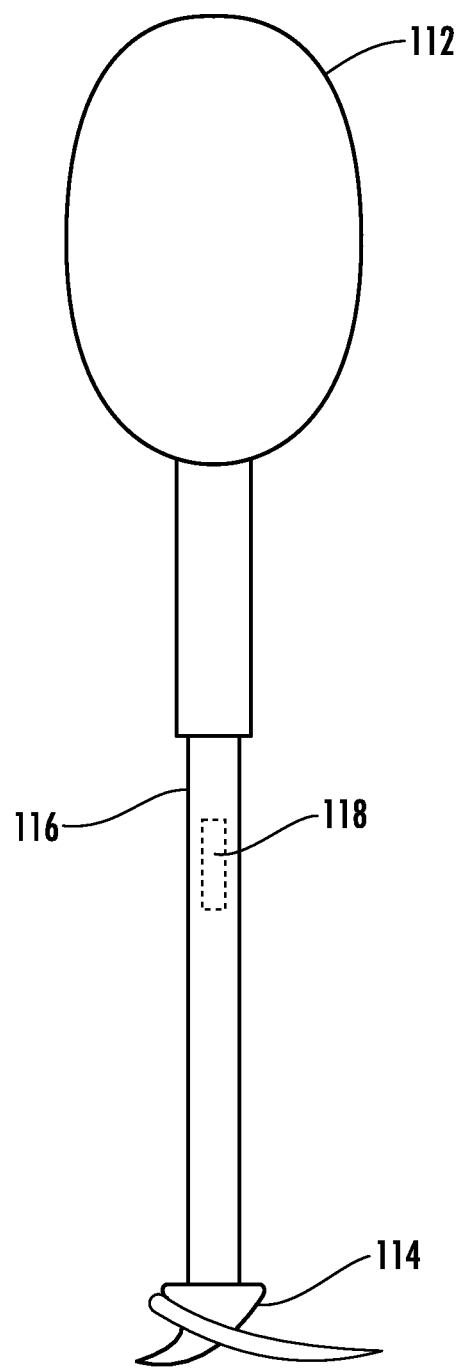
FIG. 2 shows an above knee prosthesis in an extended position. An actuator incorporated into the pylon of the prosthesis can provide lengthening and shortening of the prosthetic along the axis.
Figure 3:
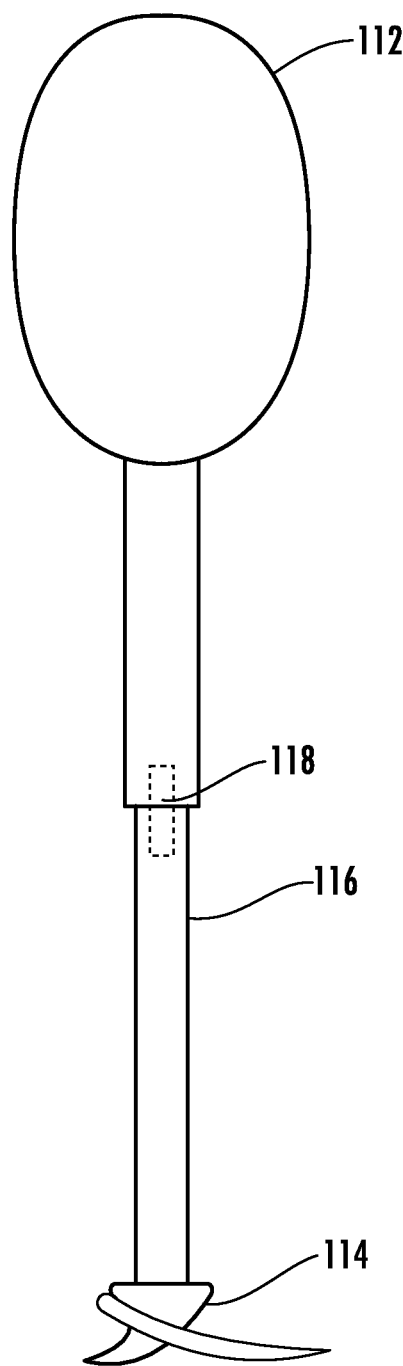
FIG. 3 shows the above knee prosthesis of FIG. 2 in a more shortened position.

FIG. 2 illustrates a prosthetic 110 for use with an above-knee amputation in an extended presentation and FIG. 3 illustrates the prosthetic 110 in a contracted orientation. As shown, the prosthetic 110 includes a proximal end 112, a distal end 114, and an actuator 118 between the two that can modify the length of the prosthetic, for instance through modification of the length of segment 116.

When utilizing a traditional prosthetic, an above-knee amputee needs to flex at the hip to accelerate the above knee portion of the prosthesis, for instance to cause flexion at a knee and provide clearance for the foot during swing phase. The amputee must then extend the hip nearing heel strike to extend an artificial knee and provide stability. These motions can be eliminated by using a prosthetic as disclosed herein. In one particular embodiment, disclosed device can eliminate the need for a rotational joint (e.g., a knee) at all and can allow the prosthetic foot to be designed for maximum efficiency. Thus, wearers with above-knee amputations can see great benefit from dynamic and automatic control over the length of the prosthesis during use.

In addition to needing to avoid a toe-strike during the swing phase of walking, the prosthesis must be stable during a static stance or during the stance phase of a gait. Traditional prosthetics typically include a mechanical knee joint to simulate natural mechanics and effectively shorten the distance from the foot to the hip by bending the prosthetic and enable the swing phase to proceed without striking the ground with the prosthetic foot. However, this artificial joint may buckle during a static stance or during ambulation, causing a fall. Moreover, a rotating artificial knee may not place the foot of the prosthesis in the proper position at the proper time for heel strike. By eliminating a knee, risk of joint buckling during a static stance or during the stance phase of a gait can be removed. A wearer may also benefit from propulsion at the end of the gait by actively lengthening the prosthesis to provide propulsion as discussed above with regard to a below-knee system.

It is not a requirement of an above-knee prosthetic that the device not include an artificial knee, however. A prosthetic knee may be incorporated in a device in conjunction with the automatic dynamic length adjustment systems. When included, an artificial knee may be passive, or the timing of the knee swing may be controlled by a control system that can be the same as or in communication with a control system of the disclosed system.

Figure 4:
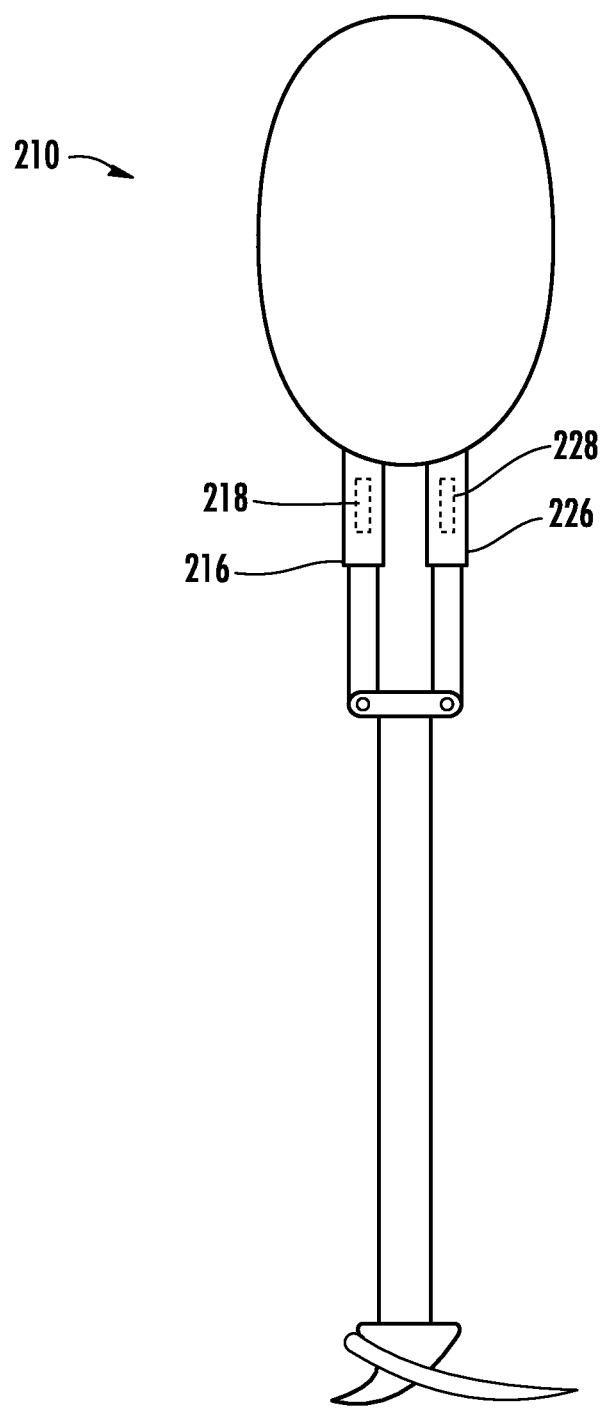
FIG. 4 shows an above knee prosthesis with two segments that can independently be extended and contracted.
Figure 5:
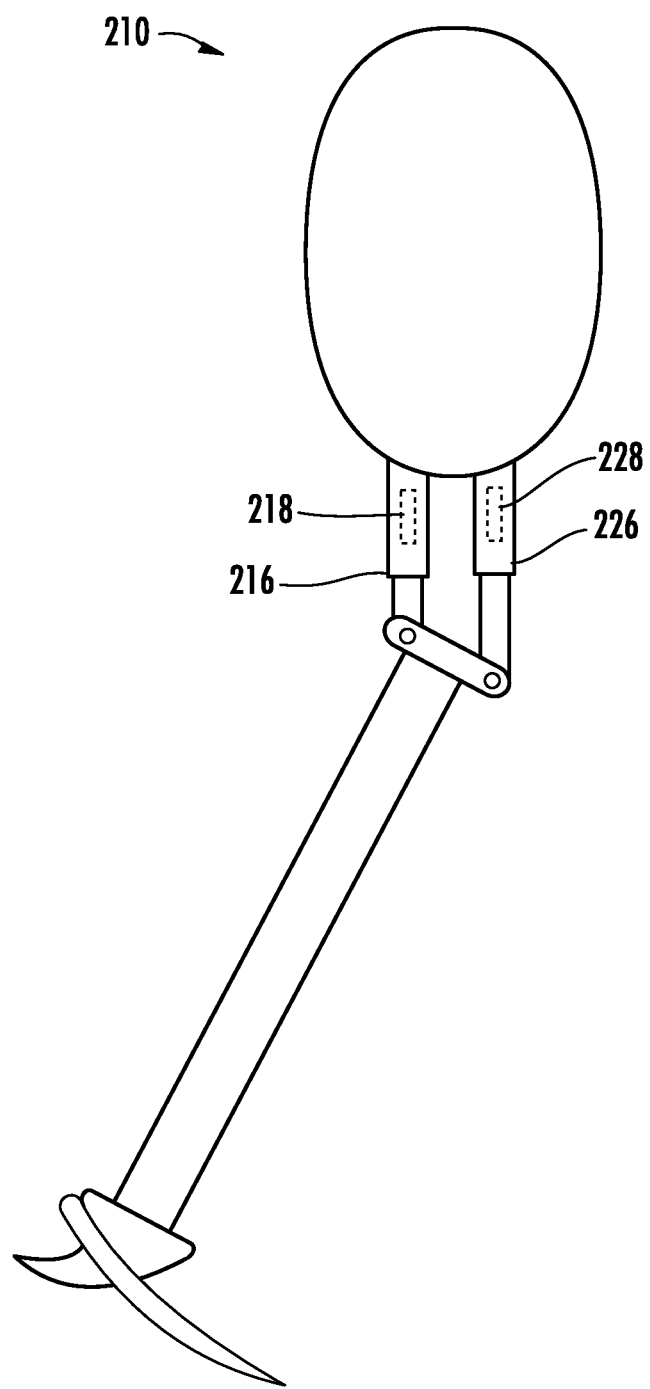
FIG. 5 shows an above knee prosthesis with two segments providing rotation around an axis simulating flexion of a knee.

In one embodiment, an automatic and dynamic system as disclosed herein can be configured to provide rotation around an axis simulating a joint generally in conjunction with a lengthening capability. By way of example, FIG. 4 and FIG. 5 illustrate a prosthetic 210 that includes two segments 216, 226 that can extend and contract together to lengthen and shorten the prosthetic as described above. In one embodiment, the two segments 216, 226 can lengthen and contract independently or antagonistically to one another to provide a rotation around an axis. FIG. 4 illustrates the prosthetic 210 with both segments 216, 226 at the same length and the prosthetic in a generally straight, axial orientation. FIG. 5 illustrates the prosthetic 210 with the segment 226 extended with respect to the segment 216. In the orientation of FIG. 5, the prosthetic 210 is thus bent, as with a knee flex.

Each segment 216, 226 can be in communication with a single control system and each can have an actuator 218, 228 to modify a length of the prosthetic. Alternatively, a single actuator can be utilized to control both segments 216, 226. Thus, a change in distance between the proximal and distal ends of the leg may be provided by two or more linear actuators providing the knee bend, or may be provided by a separate linear actuator.

Though illustrated as being parallel to one another in the embodiment illustrated in FIG. 4 and FIG. 5, it should be understood that multiple adjustable segments can be located throughout a single prosthetic. Through incorporation of multiple adjustable segments, any desired combination of motion can be combined to provide a complex pattern of movements such as extension at an angle to the axis of the prosthesis, an elliptical motion, or rotation around a moving axis.

Figure 6:
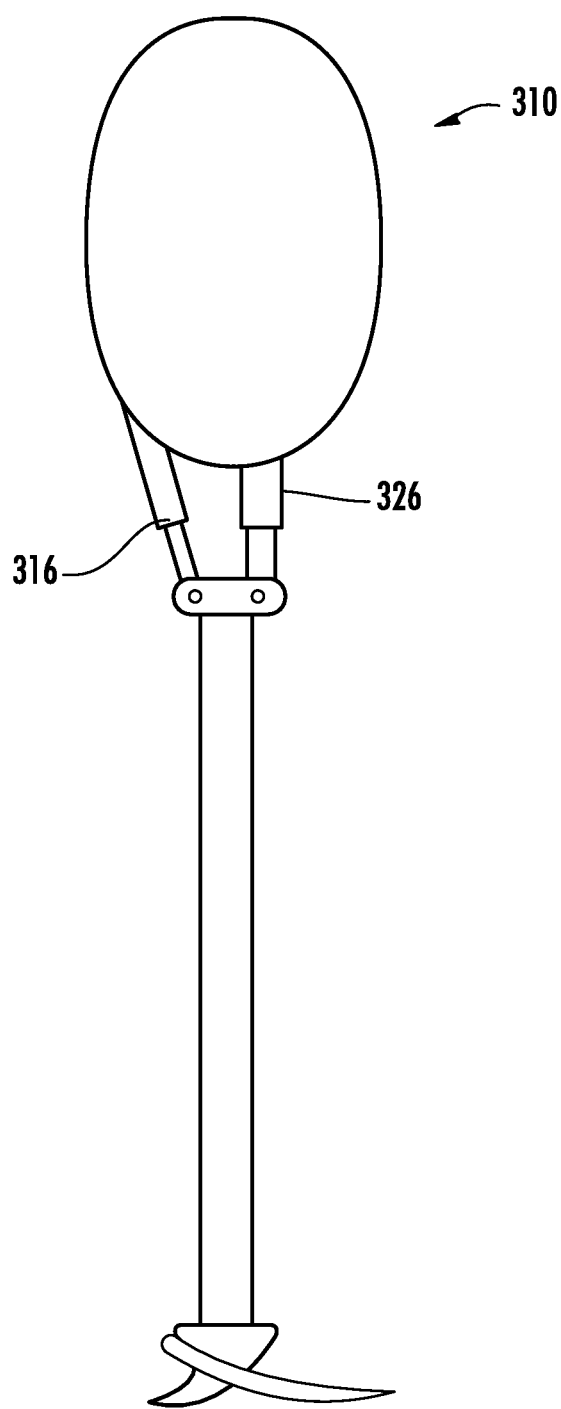
FIG. 6 shows an above knee prosthesis with a primary segment and a smaller secondary segment.

Prosthetics that include multiple adjustable segments can include segments of different sizes. For example, as illustrated in FIG. 6, a prosthetic 310 can include a first segment 316 and a second segment 326 of different widths, heights, etc. Such variations can be beneficial to provide individualized motion control to a prosthetic.

Disclosed device can be of particular benefit for high-leg amputations such as a short above-knee amputation, hip disarticulation or a hem ipelvectomy. High-leg amputees have reduced leverage against the prosthesis as well as reduced ability to control the prosthesis during the swing phase of ambulation, making ambulation much more energy intensive. With the loss of control at multiple joints as is found in high-leg amputations, the risk of falls is increased as it is more difficult to control an artificial knee as is known in prior art devices and the amputee must provide the power to advance the prosthesis. Thus, the prosthesis must be designed to minimize the risk of joint buckling and falls during the stance phase of gait.

Disclosed devices can thus be of particular benefit for high-leg amputees as the dynamic and automatic length adjustment capability can decrease the risk of fall due to joint buckling and can provide a powered motion around an axis for advancement of the prosthetic during swing phase and advancement of the body over the ground during stance phase.

The dynamic adjusting prosthesis may be of particular benefit in climbing stairs. For instance, while ascending stairs, the prosthesis may be shortened to avoid striking stairs on the upswing until heel strike, then lengthened once body weight has been transferred over the prosthesis to provide forward and upward motion. Similarly in descending stairs, the prosthesis may be lengthened to reach lower stairs, and then shorten as body weight is transferred over the prosthesis and the opposite foot is planted on a lower stair, and then shortened further to prevent striking the stairs as the prosthesis is swung forward. The use of two linear actuators to create a powered knee joint with the ability to change the articulation of the knee may be used in the exact same manner as a completely linear prosthetic, with the additional advantage of angling the foot for a more stable plant on the stair.

The prosthesis may aid standing by locking and remaining stationary at a pre-determined length, for instance as may be set by the user. The standing mode may be manually engaged by the user, or by the on-board controller utilizing a combination of accelerometers and prosthesis position sensors relative to the user.

In one embodiment, a prosthetic can provide for the adjustable segment of the prosthetic to retract beyond what may be useful during ambulation. For instance, a telescoping segment can be configured to allow for complete retraction and shorten the segment to a length of, e.g., about 18 inches or less. This mode can be convenient as it can facilitate sitting, particularly in those embodiments in which the prosthetic does not include a rotating joint, e.g., a knee. This may be particularly beneficial when sitting in a space of limited room, for instance in cars and planes where space is limited in front of the pelvis and where the full length of the un-retracted prosthetic could prevent the user from sitting.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A prosthetic lower limb comprising:
a distal end comprising a prosthetic foot;
a proximal end at a distance from the distal end, the prosthetic lower limb defining a length between the distal end and the proximal end;
at least one actuator comprising a linear extension and retraction mechanism configured to extend and retract a segment of the prosthetic lower limb between the proximal end and the distal end and thereby modify the length of the prosthetic lower limb between the distal end and the proximal end, and;
a control system in communication with the at least one actuator, the communication being configured to cyclically modify the length of the prosthetic lower limb through a single gait cycle, the single gait cycle comprising a stance phase and a swing phase, wherein the cyclic modification includes extension of the segment to increase the length of the prosthetic lower limb in preparation for heel strike on a surface, retraction of the segment to decrease the length of the prosthetic lower limb during the stance phase during which the prosthetic foot is in contact with the surface, extension of the segment to increase the length of the prosthetic lower limb at an end of the stance phase that includes immediately prior to and during a loss of contact between the prosthetic foot and the surface, and retraction of the segment to decrease the length of the prosthetic lower limb during the swing phase, wherein all extension and retraction of the segment is under the control of the actuator and the control system.

2. The prosthetic lower limb of claim 1, wherein the prosthetic lower limb is free of rotational joints.

3. The prosthetic lower limb of claim 1, wherein the prosthetic lower limb further comprises a rotational joint.

4. The prosthetic lower limb of claim 1, comprising a first actuator and a second actuator, the first and second actuator being in communication with the control system.

5. The prosthetic lower limb of claim 4, the first and second actuators being configured to operate antagonistically to one another as well as to extend and contract together to modify the length of the prosthetic lower limb.

6. The prosthetic lower limb of claim 1, further comprising a spring and/or a shock absorber.

7. The prosthetic lower limb of claim 1, wherein the prosthesis is a below-knee prosthesis, a through-knee prosthesis, an above-knee prosthesis, a hip disarticulation prosthesis, or a hemipelvectomy prosthesis.

8. The prosthetic lower limb of claim 1, the prosthetic lower limb further comprising a sensor in communication with the control system.

9. The prosthetic lower limb of claim 1, the at least one actuator comprising a ballscrew drive, an electric drive, a hydraulic drive, a pneumatic drive, or a mechanical drive.

10. The prosthetic lower limb of claim 1, the cyclic modification being configured to minimize displacement of a center of gravity of a wearer during the single gait cycle.

11. The prosthetic lower limb of claim 1, wherein the at least one actuator comprises a telescoping actuator.

12. The prosthetic lower limb of claim 1, comprising multiple segments configured for cyclic extension and retraction.

13. The prosthetic lower limb of claim 1, further comprising a locking mechanism configured to temporarily lock the prosthetic lower limb at a selected length.

14. The prosthetic lower limb of claim 8, wherein the sensor comprises an optical sensing device.

15. The prosthetic lower limb of claim 8, wherein the sensor comprising an accelerometer.

16. The prosthetic lower limb of claim 8, wherein the sensor comprises a gyroscope.

17. The prosthetic lower limb of claim 8, the sensor determining one or more of a distance from a point on the prosthesis to the surface, an angle between the segment of the prosthesis and the surface, walking speed of the prosthesis, or an impact force between the prosthesis and the surface.

18. The prosthetic lower limb of claim 8, wherein the sensor comprises a force sensor.

19. The prosthetic lower limb of claim 1, further comprising a passive impact dampener.

20. A method for forming a prosthesis, the method comprising:
   placing at least one actuator in communication with a control system;
   placing the at least one actuator in communication with a segment of a prosthetic lower limb, the prosthetic lower limb defining a length between a distal end and a proximal end of the prosthetic lower limb, the at least one actuator comprising a linear extension and retraction mechanism;
   by use of the control system, configuring the linear extension and retraction mechanism to cyclically and dynamically extend and retract the segment and thereby modify the length of the prosthetic lower limb between the distal end and the proximal end through a single gait cycle, the single gait cycle comprising a stance phase and a swing phase, wherein the cyclic and dynamic modification includes extension of the segment to increase the length of the prosthetic lower limb in preparation for heel strike on a surface, retraction of the segment to decrease the length of the prosthetic lower limb during the stance phase during which a prosthetic foot at the distal end of the prosthetic lower limb is in contact with the surface, extension of the segment to increase the length of the prosthetic lower limb at an end of the stance phase that includes immediately prior to and during a loss of contact between the prosthetic foot and the surface, and retraction of the segment to decrease the length of the prosthetic lower limb during the swing phase; wherein
   all extension and retraction of the segment is under the control of the actuator and the control system.

21. The method of claim 20, the method further comprising placing a spring and/or a shock absorber on/in the prosthesis.

22. The method of claim 20, wherein the prosthesis is a below-knee prosthesis, a through-knee prosthesis, an above-knee prosthesis, a hip disarticulation prosthesis, or a hemipelvectomy prosthesis.

* * * * *